United States Patent
Kim et al.

(10) Patent No.: US 12,268,728 B2
(45) Date of Patent: Apr. 8, 2025

(54) COMPOSITION FOR PREVENTING OR TREATING PULMONARY DISEASES COMPRISING HYALURONAN AND PROTEOGLYCAN LINK PROTEIN 1

(71) Applicant: HAPLNSCIENCE INC., Gyeonggi-do (KR)

(72) Inventors: Dae Kyong Kim, Gyeonggi-do (KR); Yong Wei Piao, Seoul (KR); Ji Min Jang, Seoul (KR); Dan Zhou, Seoul (KR); So Yoon Yun, Seoul (KR); Bo Kyung Park, Seoul (KR)

(73) Assignee: HAPLNSCIENCE, INC., Gyeonggi-do (KR)

( * ) Notice: Subject to any disclaimer, the term of this patent is extended or adjusted under 35 U.S.C. 154(b) by 951 days.

(21) Appl. No.: 17/287,443

(22) PCT Filed: Feb. 2, 2021

(86) PCT No.: PCT/KR2021/001374
§ 371 (c)(1),
(2) Date: Apr. 21, 2021

(87) PCT Pub. No.: WO2021/158000
PCT Pub. Date: Aug. 12, 2021

(65) Prior Publication Data
US 2022/0305077 A1    Sep. 29, 2022

(30) Foreign Application Priority Data
Feb. 3, 2020  (KR) .................. 10-2020-0012742

(51) Int. Cl.
A61K 38/00 (2006.01)
A23L 33/17 (2016.01)
A61K 38/17 (2006.01)
A61P 11/00 (2006.01)
C07K 14/78 (2006.01)

(52) U.S. Cl.
CPC .......... A61K 38/1709 (2013.01); A23L 33/17 (2016.08); A61P 11/00 (2018.01); C07K 14/78 (2013.01); C07K 2319/02 (2013.01); C07K 2319/21 (2013.01); C07K 2319/50 (2013.01)

(58) Field of Classification Search
CPC .......... A23L 33/17; A61P 11/00; C07K 14/78; C07K 2319/02; C07K 2319/21; C07K 2319/50
See application file for complete search history.

(56) References Cited

U.S. PATENT DOCUMENTS

| | | | |
|---|---|---|---|
| 7,908,090 B2 | 3/2011 | Kim et al. | |
| 8,030,274 B2 | 10/2011 | Kim et al. | |
| 11,202,749 B2* | 12/2021 | Kim | A61K 38/17 |
| 11,213,572 B2 | 1/2022 | Kim et al. | |
| 2008/0051680 A1 | 2/2008 | Luebcke | |
| 2008/0139500 A1 | 6/2008 | Goldberg | |
| 2008/0318967 A1 | 12/2008 | Beylin et al. | |
| 2009/0220488 A1 | 9/2009 | Gardner | |
| 2011/0112019 A1 | 5/2011 | Yamanishi et al. | |
| 2012/0128632 A1 | 5/2012 | Teumer et al. | |
| 2012/0171171 A1 | 7/2012 | West et al. | |
| 2013/0052198 A1 | 2/2013 | Milwid et al. | |
| 2014/0163118 A1 | 6/2014 | Giuliani et al. | |
| 2014/0178988 A1 | 6/2014 | West et al. | |
| 2015/0133328 A1 | 5/2015 | Ikuta et al. | |
| 2015/0157565 A1 | 6/2015 | Heartlein et al. | |
| 2015/0166624 A1 | 6/2015 | Tseng et al. | |
| 2016/0192689 A1 | 7/2016 | Horn | |
| 2016/0220699 A1 | 8/2016 | O'Heeron | |
| 2020/0000700 A1 | 1/2020 | Kim et al. | |
| 2020/0276278 A1 | 9/2020 | Kim et al. | |
| 2020/0308219 A1 | 10/2020 | Tseng et al. | |

(Continued)

FOREIGN PATENT DOCUMENTS

| | | |
|---|---|---|
| CN | 110603448 A | 12/2019 |
| EP | 2924432 A1 | 9/2015 |

(Continued)

OTHER PUBLICATIONS

Gene [Internet]. Bethesda (MD): National Library of Medicine (US), National Center for Biotechnology Information; [1988]—. Gene ID: 1404, HAPLN1 hyaluronan and proteoglycan link protein 1 [*Homo sapiens* (human)]; https://www.ncbi.nlm.nih.gov/gene/1404 (Year: 2024).*

(Continued)

*Primary Examiner* — Maria G Leavitt
*Assistant Examiner* — Michael Angelo Riga
(74) *Attorney, Agent, or Firm* — Klarquist Sparkman, LLP

(57) ABSTRACT

Provided are a recombinant hyaluronan and proteoglycan link protein 1 (HAPLN1), and a composition for preventing or treating pulmonary diseases, the composition comprising at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient. The recombinant HAPLN1 according to the present disclosure may have superior effects of improving alveolar damage caused by aging or elastin reduction, and thus may effectively prevent or treat pulmonary diseases, such as chronic bronchitis, asthma, emphysema, and chronic obstructive pulmonary disease.

8 Claims, 10 Drawing Sheets
Specification includes a Sequence Listing.

(56) References Cited

U.S. PATENT DOCUMENTS

| | | |
|---|---|---|
| 2021/0220256 A1 | 7/2021 | Yang et al. |
| 2022/0202899 A1 | 6/2022 | Kim et al. |
| 2022/0290201 A1 | 9/2022 | Kim et al. |
| 2022/0305077 A1 | 9/2022 | Kim et al. |
| 2023/0158106 A1 | 5/2023 | Kim et al. |
| 2023/0242959 A1 | 8/2023 | Kim et al. |

FOREIGN PATENT DOCUMENTS

| | | | |
|---|---|---|---|
| EP | 3677269 A1 | 7/2020 | |
| JP | 5767591 | 6/2015 | |
| JP | 2016-531147 A | 10/2016 | |
| KR | 10-2007-0112086 | 11/2007 | |
| KR | 10-2015-0053753 | 5/2015 | |
| KR | 10-2016-0143837 A | 12/2016 | |
| KR | 10-2017-0031060 | 3/2017 | |
| KR | 10-1897340 B1 | 9/2018 | |
| KR | 10-1900748 B1 | 9/2018 | |
| KR | 10-2019-0024727 | 3/2019 | |
| KR | 10-2020-0104831 A | 9/2020 | |
| RU | 2342384 C2 | 12/2008 | |
| RU | 2388504 | 5/2010 | |
| RU | 2631488 C2 | 9/2017 | |
| WO | WO 2011/006107 A1 | 1/2011 | |
| WO | WO 2011/011593 A1 | 1/2011 | |
| WO | WO 2011/126833 A2 | 10/2011 | |
| WO | WO-2013063155 A2 * | 5/2013 | ............. A61K 38/47 |
| WO | WO 2013/129456 A1 | 9/2013 | |
| WO | WO 2013/144349 A1 | 10/2013 | |
| WO | WO 2014/130411 | 8/2014 | |
| WO | WO 2016/110786 | 7/2016 | |
| WO | WO 2016/156788 A1 | 10/2016 | |
| WO | WO 2017/123951 | 7/2017 | |
| WO | WO-2018164290 A1 * | 9/2018 | ............. A23L 33/17 |
| WO | WO 2019/045451 | 3/2019 | |

OTHER PUBLICATIONS

Ecker, Brett L., et al. "Age-related changes in HAPLN1 increase lymphatic permeability and affect routes of melanoma metastasis." Cancer discovery 9.1 (2019): 82-95. (Year: 2019).*
Zanini, Andrea, et al. "The role of the bronchial microvasculature in the airway remodeling in asthma and COPD." Respiratory research 11.1 (2010): 1-11. (Year: 2010).*
Piao, Yongwei, et al. "Recombinant human hapln1 mitigates pulmonary emphysema by increasing tgf-β receptor i and sirtuins levels in human alveolar epithelial cells." Molecules and Cells 46.9 (2023): 558-572. (Year: 2023).*
Dudhia, Jayesh, Michael T. Bayliss, and Timothy E. Hardingham. "Human link protein gene: structure and transcription pattern in chondrocytes." Biochemical Journal 303.1 (1994): 329-333. (Year: 1994).*
Davis, Pamela B., and Mark J. Cooper. "Vectors for airway gene delivery." The AAPS journal 9 (2007): E11-E17. (Year: 2007).*
Orimo, Gene Delivery and Expression Series: Gene Delivery and Expression (1), Journal of Nippon Medical School, 7(2): 92-96, 2011.
Ecker et al., "Age-Related Changes in HAPLN1 Increase Lymphatic Permeability and Affect Routes of Melanoma Metastasis," Cancer Discovery, 9(1):82-95, 2019.
Zanini et al., "The role of the bronchial microvasculature in the airway remodelling in asthma and COPD," Respiratory Research, 11(1):132, 2010 (11 pages).
Office Action for KR Application No. 10-2020-0012742, dated May 26, 2020 (5 pages).
NCBI Reference Sequence NP_001875, Jan. 2, 2020 (3 pages).
Notice of Allowance for KR Application No. 10-2020-0012742, dated Aug. 27, 2020 (2 pages).
ClustalW sequence alignment, 1 page, 2022.
Haplnscience Inc., "HaplnScience Inc. 2021 Aged peoples' Health & Happiness," 17 pages, 2021.
Haplnscience Inc., "HaplnScience R&D Pipeline HS-401," 3 pages, 2021.
Ivanova et al., "Protumorigenic Role of HAPLN1 and Its IgV Domain in Malignant Pleural Mesothelioma", Clinical Cancer Research, 15(8): 2602-2611, 2009 (Author Manuscript Version).
Keire et al., "Inhibition of versican expression by siRNA facilitates tropoelastin synthesis and elastic fiber formation by human SK-LMS-1 leiomyosarcoma smooth muscle cells in vitro and in vivo," Matrix Biology, 50: 67-81, 2016.
Merrilees et al., "Changes in elastin, elastin binding protein and versican in alveoli in chronic obstructive pulmonary disease," Respiratory Research, 9: Art. No. 1, 9 pages, 2008.
Wu et al., "Deposition of insoluble elastin by pulmonary fibroblasts from patients with COPD is increased by treatment with versican siRNA," International Journal of Chronic, Obstructive Pulmonary Disease, 12: 267-273, 2017.
International Search Report and Written Opinion dated May 4, 2021 of PCT Patent Application No. PCT/KR2021/001374 (12 pages).
Huynh et al., "Hyaluronan and proteoglycan link protein 1 (HAPLN1) activates bortezomib-resistant NF-κB activity and increases drug resistance in multiple myeloma," J. Biol. Chem., 293(7): 2452-2465, 2018.
Muller et al., "Spliceosomal peptide P140 for immunotherapy of systemic lupus erythematosus: results of an early phase II clinical trial," Arthritis Rheum 58(12):3873-3883, 2008.
Sotgiu et al., "Tuberculosis Treatment and Drug Regimens," Cold Spring Harb Perspect Med. 5(5): a017822, 2015.
Blaney Davidson et al., "Reduced transforming growth factor-beta signaling in cartilage of old mice: role in impaired repair capacity," Arthritis Research & Therapy, 7:R1338-R1347, 2005.
Cheng et al., "Comparison of Gene Expression Patterns in Articular Cartilage and Dedifferentiated Articular Chondrocytes," Journal of Orthopaedic Research, 30(2): 234-245, 2012.
Czipri et al., "Genetic Rescue of Chondrodysplasia and the Perinatal Lethal Effect of Cartilage Link Protein Deficiency," Journal of Biological Chemistry, 278(40): 39214-39223, 2003.
Evanko et al., "A role for HAPLN1 during phenotypic modulation of human lung fibroblasts in vitro," Journal of Histochemistry & Cytochemistry, 68(11): 797-811, 2020.
Ganceviciene et al. "Skin anti-aging strategies" DermatoEndocrinology 4:308-319, 2012.
Govindan et al., "Haplnla is Required for Connexin43-Dependent Growth and Patterning in the Regenerating Fin Skeleton," PLoS One, 9(2): e88574, 2014 (10 pages).
Kaur et al. "Remodeling of the Collagen Matrix in Aging Skin Promotes Melanoma Metastasis and Affects Immune Cell Motility" Cancer Discovery 9:64-81, 2018.
Makrantonaki et al. "Genetics and skin aging" DematoEndocrinology 4:280-284, 2012.
Moore et al., "Fibroblast growth factor-18 stimulates chondrogenesis and cartilage repair in a rat model of injury-induced osteoarthritis," OsteoArthritis and Cartilage, 13: 623-631, 2005.
Morozumi et al., "ASB20123: A novel C-type natriuretic peptide derivative for treatment of growth failure and dwarfism," PLoS One, 14(2): e0212680, 2019 (17 pages).
Poetschke et al., "Anti-wrinkle Creams with Hyaluronic Acid: How Effective Are They?" MMW-Fortschritte der Medizin, 158(Suppl. 4): 1-6, 2016.
Tekari et al., "Transforming Growth Factor Beta Signaling Is Essential for the Autonomous Formation of Cartilage-Like Tissue by Expanded Chondrocytes," PLoS One, 10(3):e0120857, 2015 (17 pages).
Urano et al., "Single-nucleotide polymorphism in the hyaluronan and proteoglycan link protein 1 (HAPLN1) gene is associated with spinal osteophyte formation and disc degeneration in Japanese women," Eur Spine J, 20: 572-577, 2011.
Vegh et al., "Hippocarnpal Extracellular Matrix Levels and Stochasticity in Synaptic Protein Expression Increase with Age and Are Associated with Age-dependent Cognitive Decline," Molecular & Cellular Proteomics, 13(11): 2975-2985, 2014.
Wang et al., "TGFβ Signaling in Cartilage Development and Maintenance," Birth Defects Res C Embryo Today, 102(1): 37-51, 2014 (Author Manuscript version, 25 pages).

(56) References Cited

OTHER PUBLICATIONS

Watanabe and Yamada, "Mice lacking link protein develop dwarfism and craniofacial abnormalities," *Nature Genetics*, 21: 225-229, 1999.

Watanabe-Takano et al., "DA-Raf-Mediated Suppression of the Ras-ERK Pathway Is Essential for TGF-β1-Induced Epithelial-Mesenchymal Transition in Alveolar Epithelial Type 2 Cells," *PLOS ONE*, 10(5): e0127888, pp. 1-19, 2015.

\* cited by examiner

FIG. 3A

* AH: Aerosol Inhalation

| AH-1 | AH-2 | AH-3 | AH-4 |
| (No PPE/ Normal) | (PPE+saline) | (PPE+rhHAPLN1) | (PPE+HA) |

SEQUENCE LISTING

```
<160> NUMBER OF SEQ ID NOS: 1

<210> SEQ ID NO 1
<211> LENGTH: 339
<212> TYPE: PRT
<213> ORGANISM: Artificial Sequence
<220> FEATURE:
<223> OTHER INFORMATION: Recombinant human HAPLN1

<400> SEQUENCE: 1

Asp His Leu Ser Asp Asn Tyr Thr Leu Asp His Asp Arg Ala Ile His
1               5                   10                  15

Ile Gln Ala Glu Asn Gly Pro His Leu Leu Val Glu Ala Glu Gln Ala
                20                  25                  30

Lys Val Phe Ser His Arg Gly Gly Asn Val Thr Leu Pro Cys Lys Phe
            35                  40                  45

Tyr Arg Asp Pro Thr Ala Phe Gly Ser Gly Ile His Lys Ile Arg Ile
        50                  55                  60

Lys Trp Thr Lys Leu Thr Ser Asp Tyr Leu Lys Glu Val Asp Val Phe
65                  70                  75                  80

Val Ser Met Gly Tyr His Lys Lys Thr Tyr Gly Gly Tyr Gln Gly Arg
                85                  90                  95

Val Phe Leu Lys Gly Gly Ser Asp Ser Asp Ala Ser Leu Val Ile Thr
            100                 105                 110

Asp Leu Thr Leu Glu Asp Tyr Gly Arg Tyr Lys Cys Glu Val Ile Glu
        115                 120                 125

Gly Leu Glu Asp Asp Thr Val Val Ala Leu Asp Leu Gln Gly Val
    130                 135                 140

Val Phe Pro Tyr Phe Pro Arg Leu Gly Arg Tyr Asn Leu Asn Phe His
145                 150                 155                 160

Glu Ala Gln Gln Ala Cys Leu Asp Gln Asp Ala Val Ile Ala Ser Phe
                165                 170                 175

Asp Gln Leu Tyr Asp Ala Trp Arg Gly Gly Leu Asp Trp Cys Asn Ala
            180                 185                 190

Gly Trp Leu Ser Asp Gly Ser Val Gln Tyr Pro Ile Thr Lys Pro Arg
        195                 200                 205

Glu Pro Cys Gly Gly Gln Asn Thr Val Pro Gly Val Arg Asn Tyr Gly
    210                 215                 220

Phe Trp Asp Lys Asp Lys Ser Arg Tyr Asp Val Phe Cys Phe Thr Ser
225                 230                 235                 240

Asn Phe Asn Gly Arg Phe Tyr Tyr Leu Ile His Pro Thr Lys Leu Thr
                245                 250                 255

Tyr Asp Glu Ala Val Gln Ala Cys Leu Asn Asp Gly Ala Gln Ile Ala
            260                 265                 270

Lys Val Gly Gln Ile Phe Ala Ala Trp Lys Ile Leu Gly Tyr Asp Arg
        275                 280                 285

Cys Asp Ala Gly Trp Leu Ala Asp Gly Ser Val Arg Tyr Pro Ile Ser
    290                 295                 300

Arg Pro Arg Arg Arg Cys Ser Pro Thr Glu Ala Ala Val Arg Phe Val
305                 310                 315                 320
```

```
Gly Phe Pro Asp Lys Lys His Lys Leu Tyr Gly Val Tyr Cys Phe Arg
                325                 330                 335
Ala Tyr Asn
```

COMPOSITION FOR PREVENTING OR TREATING PULMONARY DISEASES COMPRISING HYALURONAN AND PROTEOGLYCAN LINK PROTEIN 1

CROSS REFERENCE TO RELATED APPLICATIONS

This application is the § 371 U.S. National Stage of International Application No. PCT/KR2021/001374, filed Feb. 2, 2021, which is based on and claims priority under 35 U.S.C. § 119 to Korean Patent Application No. 10-2020-0012742, filed on Feb. 3, 2020, in the Korean Intellectual Property Office, both of which are herein incorporated by reference in their entirety.

TECHNICAL FIELD

The present disclosure relates to a recombinant hyaluronan and proteoglycan link protein 1 (HAPLN1), and a composition for preventing or treating pulmonary diseases, the composition comprising at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient.

BACKGROUND ART

Chronic obstructive pulmonary disease (hereinafter referred to as "COPD") is the fourth leading cause of death in the world, and approximately 251 million people (4.8% of the total population of the world) suffered from COPD in 2016. It was reported that about 3.17 million people died of COPD in 2015. COPD is also more common in men than in women, and the number of patients with COPD is increasing every year.

COPD is a chronic respiratory disease that occurs more frequently than lung cancer. It is characterized by irreversible airflow obstruction and continuous progression of respiratory symptoms, such as cough, sputum, and dyspnea. It is widely known that the main causes of COPD are smoking, occupational exposure, and air pollution such as particulate matter, etc. Due to these various causes, the airflow limitation is caused by a combination of small airways disease and parenchymal destruction, leading to various clinical symptoms.

According to recent studies, aging itself may be an important cause of COPD, and has been revealed as a risk factor. In particular, COPD rapidly increases from the 50s and then increases with age, and its incidence rate in aged 60 or more is twice to three times higher than that in younger people. COPD has a profound effect on the lungs, and during this process, damage to the alveoli occurs, and gas exchange does not properly occur due to the alveolar damage. The reason why diseases do not occur in young smokers is explained by active recovery and regeneration at the same time as damage.

With the global aging trend, cell senescence, shorter telomeres, and a decrease in some anti-aging molecules cause chronic inflammation in the lungs, which may be a direct cause of emphysema known to be caused by narrowing of the small airways and disruption of elastin in the lung tissue. The pathogenesis and biochemical changes of this senile emphysema are very similar to those of common emphysema. Since emphysema is not reversible like asthma or bronchitis but irreversible, it is very difficult to treat, and there are no therapeutic or prophylactic medicines capable of effectively treating emphysema.

In particular, elastin protein, which is a component of the extracellular matrix (ECM), is a very important protein that provides elasticity and elastic recoil required for the gas exchange function of alveoli. When the alveolar wall is destroyed or damaged due to reductions in elastin production or the promotion of elastin degradation, the alveolar wall becomes unrecoverable, and thus a problem is generated in alveolar dilatation-constriction, i.e., breathing, which eventually leads to COPD.

As COPD is becoming an important global issue with the aging trend, there is a question of whether it is actually possible to treat and prevent COPD caused by aging. Until quite recently, it has been recognized that COPD is less likely to be treated or prevented, because the lungs have been known as organs that cannot be recovered or regenerated. However, as proved in the study of Butler et al. in 2012, since adult lung tissues have been demonstrated as organs that can be newly regenerated, several very recent studies have revealed, through cellular biological evidence and mechanisms, that a group of lung epithelial cells have the ability to self-differentiate and proliferate, and thus damaged or degenerated alveoli may be restored or regenerated. Accordingly, it is expected that therapeutic and prophylactic medicines will be more actively studied in the future, along with the development of technologies for regenerating and recovering degenerated alveoli.

As described above, COPD is a lung disease characterized by irreversible airflow limitation, which occurs and develops due to the airway and parenchyma destruction caused by chronic inflammation. However, COPD is known as a preventable and treatable disease, as described above. Currently, the most frequently used COPD medicines worldwide include inhaled corticosteroids (ICS) and long-acting muscarinic antagonists (LAMA), which are medicines for asthma, and long-acting β-agonists (LABA) which are medicines for chronic bronchitis and emphysema. However, these medicines do not completely treat COPD. In particular, since ICS are directly administered into the airways, they exert a strong local anti-inflammatory effect. However, systemic side effects may be increased when steroids administered into the airways are transported throughout the body from the alveoli to the blood. The side effects of these existing medicines may make patients feel nervous, and in severe cases, lead to refusal of administration, and accordingly, the development of medicines with fewer side effects is highly demanded in the market.

DESCRIPTION OF EMBODIMENTS

Technical Problem

To solve the above problems, the present disclosure provides a recombinant protein, and a superior composition for preventing or treating pulmonary diseases, the composition comprising at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient.

Additional aspects will be set forth in part in the description which follows and, in part, will be apparent from the description, or may be learned by practice of the presented embodiments of the disclosure.

Solution to Problem

A recombinant protein according to the present disclosure may be a recombinant hyaluronan and proteoglycan link protein 1 (HAPLN1) having an amino acid sequence of SEQ ID NO: 1.

A pharmaceutical composition for preventing or treating pulmonary diseases according to the present disclosure may comprise at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient.

A health functional food composition for preventing or improving pulmonary diseases according to the present disclosure may comprise at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient.

Advantageous Effects of Disclosure

The composition has few side effects, as compared with the existing therapeutic agents for pulmonary diseases, and thus it may safely and effectively prevent or treat the pulmonary diseases, which are increasing every year along with the global aging trend.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

BRIEF DESCRIPTION OF DRAWINGS

The above and other aspects, features, and advantages of certain embodiments of the disclosure will be more apparent from the following description taken in conjunction with the accompanying drawings, in which:

FIGS. 1A, 1B, and 1C show experimental results of alveoli of old mice according to one Experimental Example of the present disclosure, wherein FIG. 1A shows microscopic images of alveolar tissues after staining, and FIGS. 1B and 1C show graphs showing quantification of alveoli density, in FIGS. 1A, 1B, and 1C, 'Young-saline' represents a group prepared by administering phosphate buffered saline (PBS) to a normal control group (Young group), 'Old-saline' represents a group prepared by administering PBS to an old control group (Old group), and 'Old-rhHAPLN1' represents a group prepared by administering rhHAPLN1 diluted in PBS to an old rhHAPLN1-treated group (Old+rhHAPLN1 group);

FIGS. 3A, 3B, and 3C show experimental results of aerosol inhalation groups (AH groups) according to one Experimental Example of the present disclosure, wherein FIG. 3A shows microscopic images of alveolar tissues of each group after staining, and FIGS. 3B and 3C show graphs showing the results of measuring mean linear intercepts (MLI) thereof; and FIGS. 4A, 4B, and 4C show experimental results of intratracheal instillation groups (TI groups) according to one Experimental Example of the present disclosure, wherein FIG. 4A shows microscopic images of alveolar tissues of each group after staining, and FIGS. 4B and 4C show graphs showing the results of measuring MLI thereof.

SEQUENCES

Figure 1A:
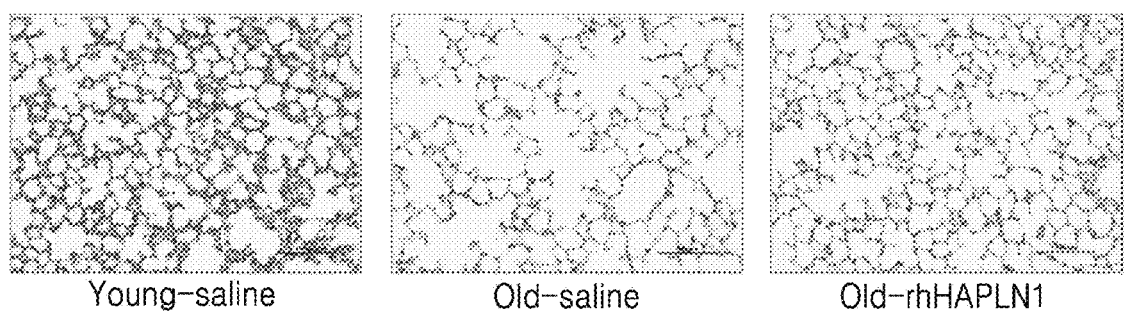

The Sequence Listing is submitted as an ASCII text file, created on Apr. 15, 2021, 3328 bytes, which is incorporated by reference herein in its entirety.

MODE OF DISCLOSURE

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in detail.

The present inventors have produced a recombinant hyaluronan and proteoglycan link protein 1 (HAPLN1), and demonstrated its effect of improving alveolar damage and its therapeutic effect in a chronic obstructive pulmonary disease animal model, thereby completing the present disclosure.

As used herein, the term "preventing" refers to all of actions by which the occurrence of pulmonary diseases or one or more symptoms thereof are restrained or retarded by administering the pharmaceutical composition or the health functional food composition according to the present disclosure. Further, it includes treatment of a subject with regression of the disease to prevent or avoid recurrence.

As used herein, the term "treating" refers to all of actions by which pulmonary diseases or one or more symptoms thereof have taken a turn for the better or been modified favorably, such as being alleviated, reduced, and extinguished, by administering the pharmaceutical composition according to the present disclosure.

As used herein, the term "improving" refers to all of actions by which pulmonary diseases or one or more symptoms thereof have taken a turn for the better or been modified favorably, such as being alleviated, reduced, and extinguished, by intaking the health functional food composition according to the present disclosure.

As used herein, the term "pharmaceutical composition" refers to a composition administered for a specific purpose, and with respect to the objects of the present disclosure, the pharmaceutical composition refers to a composition administered to prevent or treat pulmonary diseases or one or more symptoms thereof.

As used herein, the term "health functional food" refers to a food produced or processed using functional raw materials or ingredients which are beneficial to the human body in compliance with the HEALTH FUNCTIONAL FOODS Act No. 6727, and refers to a food having high medical and medicinal effects, which is processed to efficiently exhibit bio-regulatory functions such as prevention or improvement of pulmonary diseases, biological defense, immunity, and recovery, with respect to the objects of the present disclosure, in addition to supplying nutrients.

The present disclosure provides a recombinant hyaluronan and proteoglycan link protein 1 (HAPLN1) having an amino acid sequence of SEQ ID NO: 1.

The "HAPLN1" is a protein that stabilizes hyaluronic acid by linking hyaluronic acid to proteoglycans, and is a constituent protein in the extracellular matrix, which was first discovered in joints of vertebrates.

The "recombinant HAPLN1" according to the present disclosure is a recombinant protein prepared by using the HAPLN1.

The present disclosure provides a pharmaceutical composition for preventing or treating pulmonary diseases, comprising: at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient.

In certain embodiments, the HAPLN1 protein provided herein may comprise an amino acid sequence having at least 95% sequence identity with SEQ ID NO:1. In certain of these embodiments, the HAPLN1 protein may comprise an amino acid sequence with at least 95%, at least 96%, at least 97%, at least 98%, at least 99%, or at least 99.5% sequence identity to the amino acid sequence set forth in SEQ ID NO: 1. Also, the polypeptide disclosed in the specification may include a peptide of SEQ ID NO: 1, a fragment thereof, and a peptide in which at least one, two, three, four, five, six, or seven amino acids are modified.

As used herein, the term "identity," is a relationship between two or more polypeptide sequences, as the case may be, as determined by comparing the sequences. In the art, "identity" also means the degree of sequence relatedness between polypeptide sequences, as the case may be, as determined by the match between strings of such sequences. "Identity" can be readily calculated by known methods, such as for example using BLAST (National Center for Biological Information (NCBI) Basic Local Alignment Search Tool) version 2.2.1 software with default parameters.

In certain embodiments, some amino acids in a peptide that makes physicochemical characteristics of the polypeptide of SEQ ID NO: 1 changed may be modified within the scope of the present invention. For example, amino acids may be modified to allow the peptide to have enhanced enzymatic, chemical, or thermal stability, changed substrate specificity, and shifted optimal pH.

The recombinant HAPLN1 may have the effect of improving alveolar damage caused by aging or elastin reduction, and therefore, it may be used as a pharmaceutical composition for preventing or treating pulmonary diseases. Further, according to one Experimental Example of the present disclosure, it was confirmed that the recombinant HAPLN1 exhibits significant therapeutic effects in a chronic obstructive pulmonary disease animal model.

As used herein, the term "agent" refers to any substance, including, but not limited to, a chemical compound, a small molecule, an antibody, peptide mimetic, peptide or protein.

As used herein, the term "an effective agent" refers to HAPLN1 expression promoting agent which promotes the expression of HAPLN1 protein or gene; or HAPLN1 activating agent which activates the functions of HAPLN1 protein or gene. The effective agent as used herein includes a variety of compounds, proteins or peptides, base sequences, and the like which are capable of enhancing the expression of HAPLN1 gene; or HAPLN1 protein and/or a fragment thereof, or activating the functions of HAPLN1 protein or gene. The activating agent also includes a variety of metabolites, precursors, or pharmaceutical equivalents of the compounds, proteins or peptides, or base sequences.

In the pharmaceutical composition according to the present disclosure, the pulmonary disease may be one or more selected from the group consisting of chronic bronchitis, asthma, emphysema, and chronic obstructive pulmonary disease (COPD), but is not limited thereto, and the pulmonary disease may include various diseases caused by lung damage.

The pharmaceutical composition according to the present disclosure may be prepared according to a common method in the pharmaceutical field. In addition to the active ingredient, the pharmaceutical composition may be blended with an appropriate pharmaceutically acceptable carrier depending on a formulation, and may further include excipients, diluents, dispersants, emulsifiers, buffers, stabilizers, binders, disintegrants, solvents, etc., if necessary. The appropriate carriers are those that do not hinder the activity and property of the recombinant HAPLN1 according to the present disclosure, and may be differently selected depending on the dosage form and formulation.

The pharmaceutical composition according to the present disclosure may be applied in any dosage form, and more specifically, may be formulated into oral dosage forms, or parenteral dosage forms such as external preparations, suppositories and sterile injectable solutions according to a common method.

Among the oral dosage forms, the solid dosage form may be in the form of tablets, pills, powders, granules, capsules, etc., and may be prepared by mixing with at least one of excipients, for example, starch, calcium carbonate, sucrose, lactose, sorbitol, mannitol, cellulose, gelatin, etc. In addition to simple excipients, lubricants such as magnesium stearate, talc, etc. may also be included. In addition, the capsule dosage form may further include a liquid carrier such as fatty oil, in addition to the above-mentioned substances.

Among the oral dosage forms, liquid dosage forms correspond to suspensions, liquid solutions for internal use, emulsions, syrups, etc. In addition to water and liquid paraffin, which are commonly used simple diluents, various excipients such as wetting agents, sweetening agents, fragrances, preservatives, etc. may be included.

The parenteral dosage forms may include a sterile aqueous solution, a non-aqueous solvent, a suspension, an emulsion, a lyophilized formulation, and a suppository. As the non-aqueous solvent and suspension, propylene glycol, polyethylene glycol, vegetable oils such as olive oil, injectable esters such as ethyl oleate, etc. may be used. As a base for suppositories, witepsol, macrogol, Tween 61, cacao butter, laurin butter, glycerogelatin, etc. may be used. The present disclosure is not limited thereto, and any appropriate formulation known in the art may be used.

To the pharmaceutical composition according to the present disclosure, calcium or vitamin $D_3$ may be further added to enhance therapeutic efficacy.

The pharmaceutical composition according to the present disclosure may be administered in a pharmaceutically effective amount.

As used herein, the term "pharmaceutically effective amount" refers to an amount which is sufficient to apply for treatment of diseases at a reasonable benefit/risk ratio applicable to any medical treatment and does not cause adverse effects.

The effective dosage level of the pharmaceutical composition may be determined, depending on factors, including the purpose of use, a patient's age, sex, body weight, and health conditions, the kind and severity of the disease, drug activity, drug sensitivity, administration method, administration time, administration route, excretion rate, the duration of treatment, drugs used in combination or used concurrently, and other factors known in the medical field. For example, although not constant, the pharmaceutical composition may be generally administered in an amount of 0.001 mg/kg to 100 mg/kg, preferably, 0.01 mg/kg to 10 mg/kg once to several times a day. The administration dosage does not limit the scope of the present disclosure in any aspect.

The pharmaceutical composition according to the present disclosure may be administered to any animal that may develop pulmonary diseases, and the animal may include, for example, humans and primates, as well as livestock such as cattle, pigs, horses, dogs, etc.

The pharmaceutical composition according to the present disclosure may be administered via an appropriate administration route according to the formulation type, and may be administered via various routes, either oral or parenteral route, as long as it may reach a target tissue. The administration method is not particularly limited, but the administration may be made by a common method, for example, orally, rectally, intravenously, intramuscularly, or local application, subcutaneously, respiratory inhalation, endometrial, or intracerebroventricular injection.

The pharmaceutical composition according to the present disclosure may be used alone, or may be used in combination with surgery or other chemical treatment for the prevention or treatment of pulmonary diseases.

Further, the present disclosure provides a health functional food composition for preventing or improving pulmonary diseases, the health functional food composition comprising at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient.

In certain embodiments, the HAPLN1 protein provided herein may comprise an amino acid sequence having at least 95% sequence identity with SEQ ID NO:1. In certain of these embodiments, the HAPLN1 protein may comprise an amino acid sequence with at least 95%, at least 96%, at least 97%, at least 98%, at least 99%, or at least 99.5% sequence identity to the amino acid sequence set forth in SEQ ID NO: 1. Also, the polypeptide disclosed in the specification may include a peptide of SEQ ID NO: 1, a fragment thereof, and a peptide in which at least one, two, three, four, five, six, or seven amino acids are modified.

The recombinant HAPLN1 may have the effect of improving alveolar damage caused by aging or elastin reduction, and therefore, it may be used as a health functional food composition for preventing or improving pulmonary diseases.

In the health functional food composition according to the present disclosure, the pulmonary disease may be one or more selected from the group consisting of chronic bronchitis, asthma, emphysema, and chronic obstructive pulmonary disease (COPD), but is not limited thereto, and the pulmonary disease may include various diseases caused by lung damage.

In the health functional food composition according to the present disclosure, the health functional food may be prepared in powder, granules, tablets, capsules, syrups, beverages, etc. for preventing or improving pulmonary diseases, and there is no limitation in the form of the food, and it may include all the foods of the usual meaning. For example, the food may include beverages and various drinks, fruits and processed foods thereof (canned fruits, jams, etc.), fish, meat and processed foods thereof (ham, bacon, etc.), breads and noodles, cookies and snacks, dairy products (butters, cheeses, etc.), etc., and may include all the functional foods of the usual meaning. Further, the food may include a food used as a feed for animals.

The health functional food composition according to the present disclosure may be prepared by further including a food additive acceptable for use in food, and other suitable auxiliary ingredients, which are commonly used in the art.

The suitability of the food additives is determined by the specification and standard of the concerned item in accordance with the General Rules and General Test of the Korean Food Additives Code authorized by the Korean Ministry of Food and Drug Safety, unless otherwise specified. The items listed in the above 'Food Additives Code' are, for example, synthetic additives such as ketones, glycine, potassium citrate, nicotinic acid, cinnamic acid, etc.; natural additives such as persimmon color, licorice extract, microcrystalline cellulose, kaoliang color, guar gum, etc.; and mixture additives such as L-sodium glutamate, alkali additives for noodles, preservatives, tar colors, etc.

Other auxiliary ingredients may further include, for example, flavors, natural carbohydrates, sweeteners, vitamins, electrolytes, colorants, pectic acids, alginic acids, organic acids, protective colloidal thickeners, pH adjusters, stabilizers, preservatives, glycerin, alcohols, carbonating agents, etc. In particular, as the natural carbohydrate, monosaccharides such as glucose and fructose, disaccharides such as maltose and sucrose, polysaccharides such as dextrin and cyclodextrin, sugar alcohol such as xylitol, sorbitol, erythritol, etc. may be used. Examples of the sweeteners may include natural sweeteners such as thaumatin and stevia extract, or synthetic sweeteners such as saccharin and aspartame, etc.

The effective dose of the recombinant HAPLN1 included in the health functional food according to the present disclosure may be appropriately adjusted according to the purpose of use, such as prevention or improvement of pulmonary diseases. Since the composition includes a food as a raw material, it has advantages of being free from side effects that may occur when general drugs are taken for a long period of time. The composition is also excellent in portability, and therefore, it may be taken as a supplement agent for preventing or improving pulmonary diseases.

Hereinafter, the present disclosure will be described in detail with reference to exemplary embodiments for better understanding. However, the following exemplary embodiments are only for illustrating the present disclosure, and the scope of the present disclosure is not limited to the following exemplary embodiments. The exemplary embodiments of the present disclosure are provided to more fully explain the present disclosure to a person of ordinary skill in the art.

Further, the present disclosure may provide a method of preventing or treating pulmonary diseases in a subject in need thereof, the method comprising administering to a subject a pharmaceutical composition according to the present disclosure.

The subject is preferably a mammal, including humans and may be patients in need of treatment for pulmonary diseases. The patient may include patients undergoing pulmonary disease treatment, patients who have been subjected to pulmonary disease treatment, and patients in need of treatment of pulmonary disease, and also patients who have undergone surgical operations to treat pulmonary disease. Administering the pharmaceutical composition according to the present disclosure to an individual may allow the pulmonary disease to be alleviated or treated.

As used herein, the term "alleviation" refers to any action in which pulmonary disease is reduced via or benefits from administration of the pharmaceutical composition in accordance with the present disclosure. The pharmaceutical composition according to the present disclosure is administered in a pharmaceutically effective amount.

As used herein, the term "administration" refers to the introduction of a pharmaceutical composition according to the present disclosure to a subject using any suitable method. Routes of administration may include, but not limited to, intratracheal or intrabronchial instillation or by inhalation, or any types of injections, or any types of oral medication, or any types of transdermal medication. As one of examples, the pharmaceutical composition may be administered in the form of an aerosol or may be administered by instillation.

Administration of the pharmaceutical composition according to the present disclosure may be performed by aerosol, which can be generated by a nebulizer, or by instillation. The pharmaceutical composition may be administered alone, or with a carrier such as saline solution, DMSO, an alcohol, or water. It may also be used as a vehicle for the intratracheal administration of various agents, such as those, which prevent degradation of elastic fibers or promote their resynthesis. The effective daily amount of the composition is from about 0.001 mg/kg to 100 mg/kg, preferably, 0.01 mg/kg to 10 mg/kg of body weight. The administration dosage does not limit the scope of the present disclosure in any aspect. For example, the amount of pharmaceutical composition intratracheally administered daily to a human being may vary from about 0.001 mg/kg to about 100 mg/kg of body weight. Preferably, the daily amount is from about 0.01 mg/kg to about 10 mg/kg body weight of the human being treated (daily).

Further, the time over which the pharmaceutical composition is administered may vary as is well known in the art to achieve the desired results. For example, the pharmaceutical composition may be administered as an aerosol from about 30 seconds to about 1 hour per treatment regimen, 1 to 5 times daily, or until the desired daily dosage is fully administered.

In addition, the pharmaceutical composition for preventing or treating pulmonary diseases, comprising: at least one selected from the group consisting of HAPLN1 (hyaluronan and proteoglycan link protein 1) protein, a gene coding for the HAPLN1 protein, and an effective agent for promoting the expression or activating the functions of HAPLN1 protein or gene as an active ingredient according to the present disclosure may be administered simultaneously/sequentially in combination with other existing drugs for the treatment of pulmonary diseases or with existing treatment methods thereof. Such administration may be single or multiple administration. It is important to administer an amount that will achieve the maximum effect with a minimum amount without side effects while taking into account all the factors. The amount may be easily determined by those skilled in the art.

<Example 1> Production of Recombinant Human HAPLN1 (rhHAPLN1)

1. Amino Acid Sequence of Recombinant Human HAPLN1

An amino acid sequence constituting a recombinant HAPLN1 is as follows:

(SEQ ID NO: 1)
DHLSDNYTLDHDRAIHIQAENGPHLLVEAEQAKVFSHRGGNVTLPCKFYR

DPTAFGSGIHKIRIKWTKLTSDYLKEVDVFVSMGYHKKTYGGYQGRVFLK

GGSDSDASLVITDLTLEDYGRYKCEVIEGLEDDTVVVALDLQGVVFPYFP

RLGRYNLNFHEAQQACLDQDAVIASFDQLYDAWRGGLDWCNAGWLSDGSV

QYPITKPREPCGGQNTVPGVRNYGFWDKDKSRYDVFCFTSNFNGRFYYLI

HPTKLTYDEAVQACLNDGAQIAKVGQIFAAWKILGYDRCDAGWLADGSVR

YPISRPRRRCSPTEAAVRFVGFPDKKHKLYGVYCFRAYN

2. Expression, Purification, and Preservation of Recombinant Human HAPLN1 (rhHAPLN1) Protein To prepare the rhHAPLN1 protein (gene number 2678736), a DNA vector encoding the amino acid sequence of the rhHAPLN1 was transfected into Expi™ 293 cell (ThermoFisher Scientific Co., Waltham, MA, USA) as a host cell. For purification, a secretory signal peptide, 10 histidines (H, His), and TEV protease-recognition site were inserted into the amino-terminus, and expressed. 3 days after transfection of the vector, the culture medium was collected, and purified through a HisTrap column (GE Healthcare, IL, USA), and then the TEV protease-recognition site was cleaved by TEV protease, and molecules including histidine were removed using DynaBeads (Thermo Fisher Scientific). The solution thus obtained was subjected to dialysis using 40 mM Tris-HCl and 1 M NaCl at pH 8.0 for 16 hr. A protein concentration of the final purification product was 0.11 mg/ml, and aliquoted into a single dose using 20 mM Tris-HCl, 0.5 M NaCl at pH 8.0, 50% glycerol as a solvent, and then stored in a refrigerator at −20° C. before use.

<Experimental Example 1> Examination of Effect of Improving Alveolar Architecture in Old Mice by Repeated Intraperitoneal Administration of rhHAPLN1

1. Preparation and Rearing of Experimental Animals

As for experimental animals, 2-month-old male C57BL/6J (Young Bio Co., Ltd., Korea) mice were determined as a young mouse, and 20-month-old male C57BL/6J mice were determined as an old mouse. The animals were allowed free access to water and feed, and the breeding room was maintained at a temperature of 21° C. to 24° C., humidity of 40% to 60%, and 12 light/12 dark cycle.

Five young mice were assigned to a normal control group (Young group), and each five old mice were assigned to an old control group (Old group) and an old rhHAPLN1-treated group (Old+rhHAPLN1 group). rhHAPLN1 diluted in phosphate buffered saline (PBS) was intraperitoneally injected to the old rhHAPLN1-treated group (Old+rhHAPLN1 group) (IP injection) at a dose of 0.1 mg/kg with a volume of 80 μl once, which was performed 3 times a week for a total of 3 weeks. The other two control groups were administered with the equal amount of PBS in the same manner.

2. Staining and Microscopic Observation of Alveolar Tissue

At the end of the experiment, cardiac perfusion was performed, and then the left lung was bisected into upper and lower parts, and fixed with neutral buffered 10% formalin (NBF), and paraffin tissue sections were prepared so that the cross section of the upper piece was visible. Tissue sections were stained by a hematoxylin & eosin (H&E) method, and photographed using a Ni-U (Nikon) microscope and a DS-Ri1 (Nikon) digital camera, and the results are shown in FIG. 1(A) (Scale bar=100 μm).

In addition, with respect to the stained tissue sections of each individual, mean linear intercepts (MLIs) were calculated using the Image J program to quantify alveolar density. The higher MLI value indicates the lower surface area of alveoli, and is used as an index indicating severity of emphysema or chronic obstructive pulmonary disease (COPD). The Equation is Lm (μm)=number of intersections/ (grid length (μm)×number of lines). After measuring the average value of three random areas per animal, statistical analysis was performed for the values of five animals using Sigma plot 12.0 and Graph Pad Prism 8. The results are shown in FIG. 1(B).

Figure 1B:
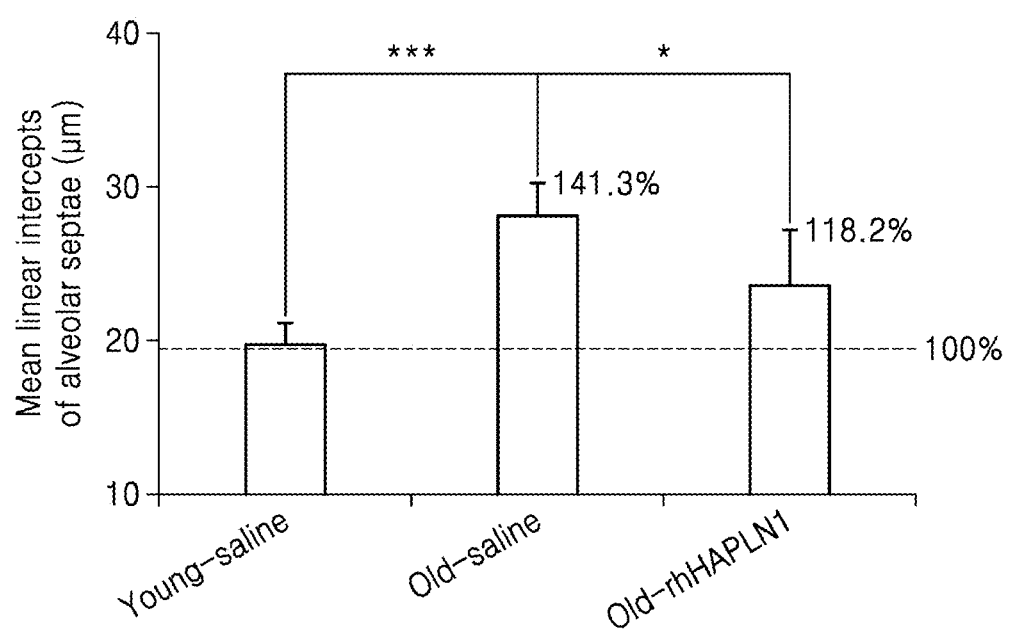
Figure 1C:
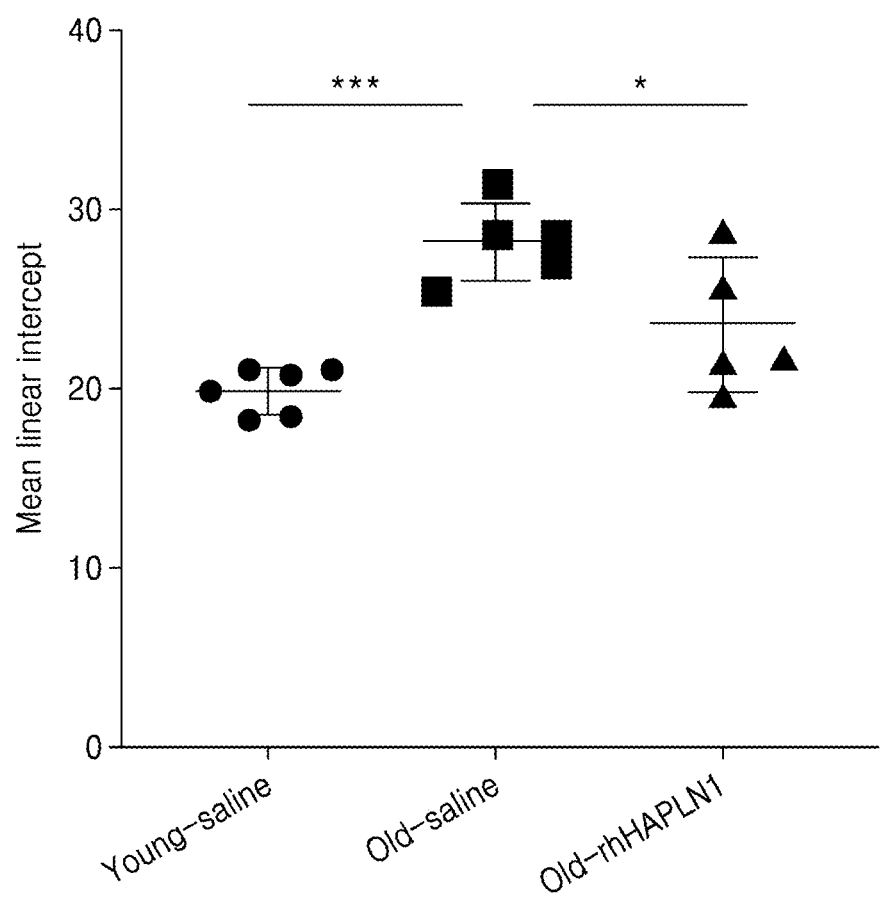

As shown in FIGS. 1(A) and 1(B), alveoli MLI values (μm) of old mice increased by about 141%, as compared with those of young mice (p<0.001). Meanwhile, this increase due to the cause of aging itself was found to be reduced by about 56% by treatment with rhHAPLN1 (p<0.0435).

<Experimental Example 2> Efficacy of rhHAPLN1 in Porcine Pancreatic Elastase (PPE)-Induced COPD Model 1. Preparation and Rearing of Experimental Animals As for experimental animals, 6 to 10 week-old-female C57BL6/ N (Young Bio, Republic of Korea) mice weighing 20 g to 25 g were used, and the mice were divided into five mice per group. The animals were allowed free access to water and feed, and the breeding room was maintained at a temperature of 21° C. to 24° C., humidity of 40% to 60%, and 12 light/12 dark cycle.

2. Induction of COPD

A COPD-induced mouse model was prepared with reference to Suki et al (2017, Methods Mol. Biol. 1639:67-75) and Wright et al (2008, Am J Physiol Lung Mol Physiol 295: L1-L15).

To inhale elastase into the lungs, porcine pancreatic elastase (EC134; PPE) was first purchased from Elastin Products Company Inc. (Owensville, Missouri, USA), and 6 IU/30 μl thereof was administered once per animal a day before drug treatment. The administration was performed by dividing animals into two groups according to the inhalation method.

In detail, an aerosol inhalation group (AH) was orally administered using a 20 G (0.9×50 mm) oral zonde needle. It was administered by carefully opening the mouth, pulling the tongue, dropping the elastase solution on the back thereof, i.e., on the distal oropharynx, and at the same time, blocking both nostrils to induce inhalation. Meanwhile, an intratracheal instillation (TI) group was administered by inducing spontaneous inhalation of mice by instilling in the nasal cavity using an Eppendorf pipette. The mice were weighed twice a week, and each group was divided into four subgroups for administration of the composition drug.

3. Efficacy of Composition Drug

The AH group was subdivided into AH-1: No PPE treat (normal) group, AH-2: PPE+saline group, AH-3: PPE+ rhHAPLN1 group, and AH-4: PPE+hyaluronic acid (HA) group, and the TI group was subdivided into TI-1: No PPE treat (normal) group, TI-2: PPE+saline group, TI-3: PPE+ rhHAPLN1 group, and TI-4: PPE+HA group. Here, HA represents hyaluronic acid, which was used as a positive control, because it is known to be effective against COPD. Administration and concentration of HA were determined with reference to Cantor et al (2005, Experimental Lung Research, 31:417-430), and accordingly, a *Streptococcus equi*-derived hyaluronic acid sodium salt (Sigma-Aldrich; St. Louis, MO, USA, Cat. 73641-10MG) was purchased and used.

Figure 2:
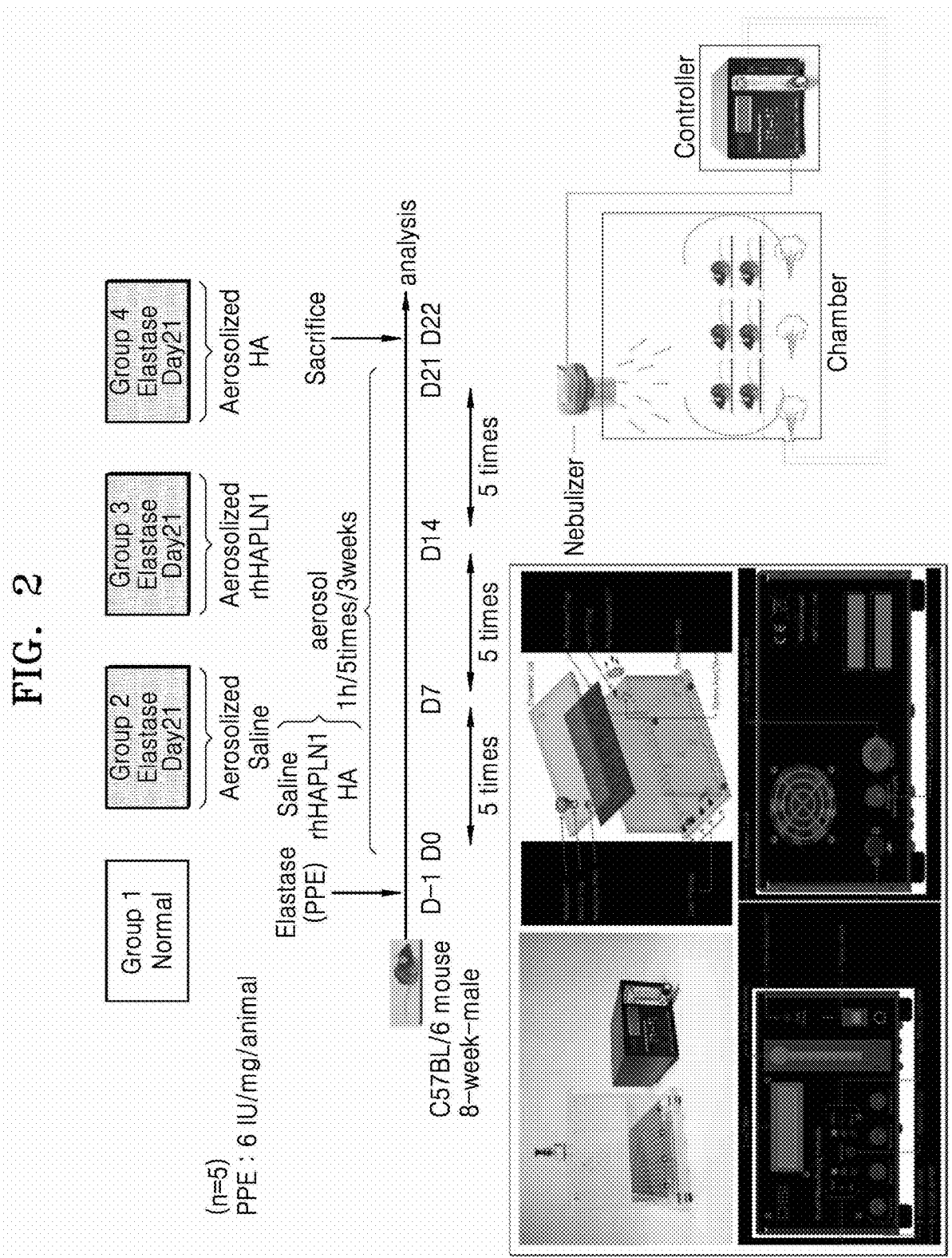
FIG. 2 shows a schematic illustration of aerosolization according to one Experimental Example of the present disclosure.

Each pharmaceutical composition sample was administered five times a week using a Mass Dosing System, specifically, an aerosol chamber (Data Science International) for aerosolization from 1 day after elastase administration (Ball flow meter 3, aerosol 1 hour, duty 30%). A schematic illustration of the aerosolization is shown in FIG. 2.

Each sample was aerosolized with an aerosolizer at a concentration of 0.33% (w/v) rhHAPLN1 and 5.71% (w/v) HA by adjusting its volume to 6.8 ml per single administration using physiological saline as a solvent, and 1 day after the last aerosolization on the $21^{st}$ day, cardiac perfusion was performed under anesthesia. Then, the left lung was bisected horizontally, and the lower part was taken, and fixed with neutral buffered 10% formalin (NBF), and a paraffin tissue section was prepared so that the cross section of the upper piece was visible. Tissue sections were stained by a hematoxylin & eosin (H&E) method, and photographed using a Ni-U (Nikon) microscope and a DS-Ri1 (Nikon) digital camera at 200× magnification to obtain image data of the alveolar tissue (Scale bar=100 μm), and MLI of the alveoli was measured. The higher MLI value indicates the lower surface area of alveoli, and is used as an index indicating the severity of emphysema or COPD. The Equation is Lm (μm)=number of intersections/(grid length (μm)× number of lines). After measuring the average value of three random areas per animal, statistical analysis was performed for the values of five animals using Sigma plot 12.0 and Graph Pad Prism 8.

Experimental results of AH groups are shown in FIG. 3, and experimental results of TI groups are shown in FIG. 4.

Figure 3B:
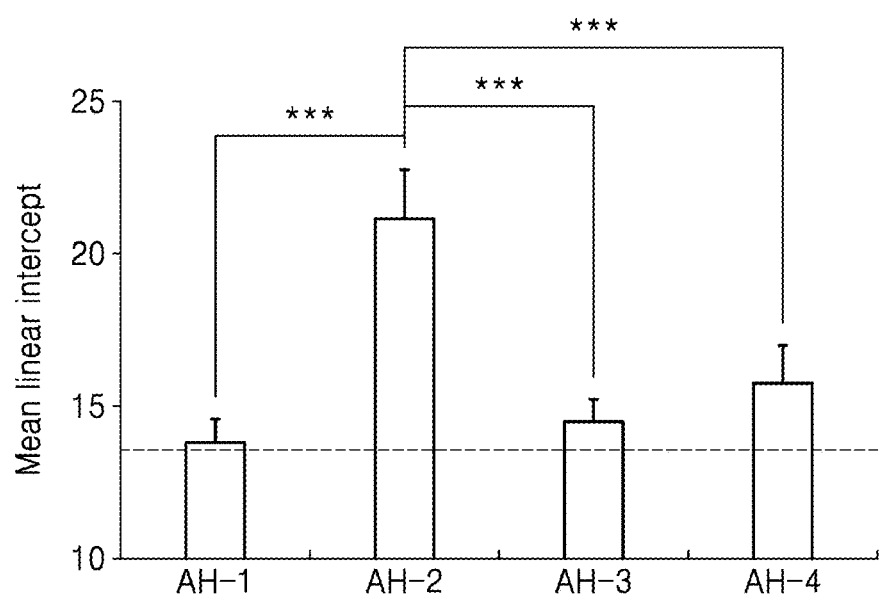
Figure 3C:
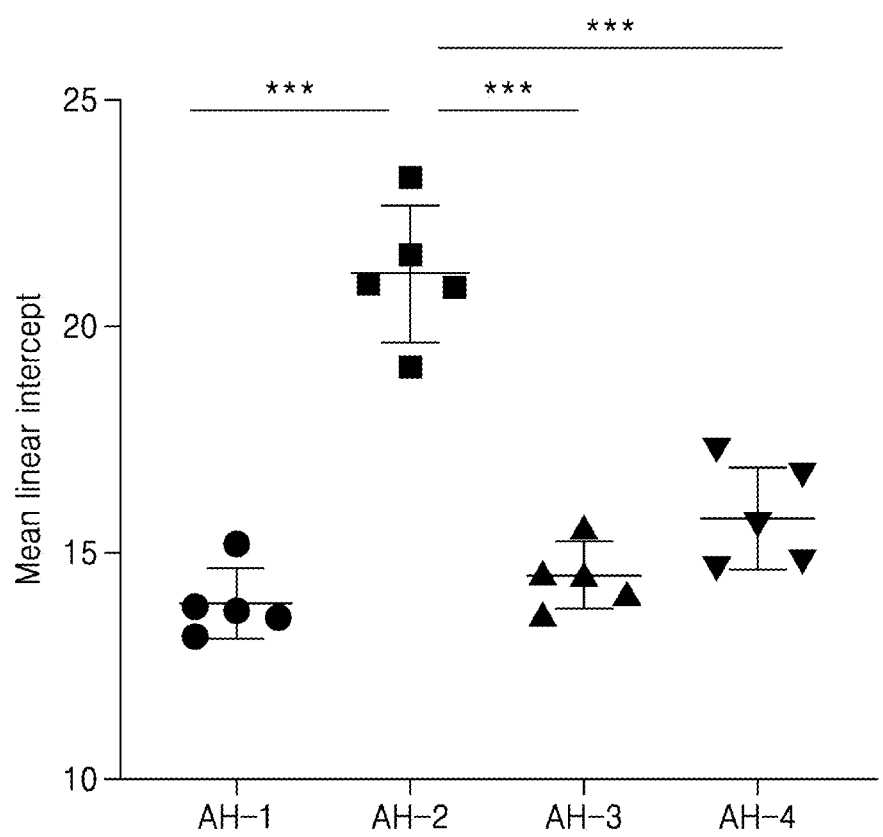

FIG. 3 shows the results of AH groups, and referring to FIGS. 3A to 3C, the PPE-treated group (AH-2) of 21.2 μm showed about 1.5 times increase, as compared with the untreated normal group (AH-1) of 13.8 μm (p<0.001). The rhHAPLN1-treated group (AH-3) of 14.5 μm showed about 95% reduction, as compared with the PPE-treated group of 21.2 μm (p<0.00002), indicating almost recovery to a normal state.

In contrast, from the viewpoint of concentration, the HA-treated group (AH-4) of 5.71% (w/v) which was about 17 times higher than 0.33% (w/v) showed about 73% reduction (p<0.002), indicating that the positive control HA treatment showed slightly lower efficacy than the rhHAPLN1 treatment which showed about 95% reduction.

Figure 4A:
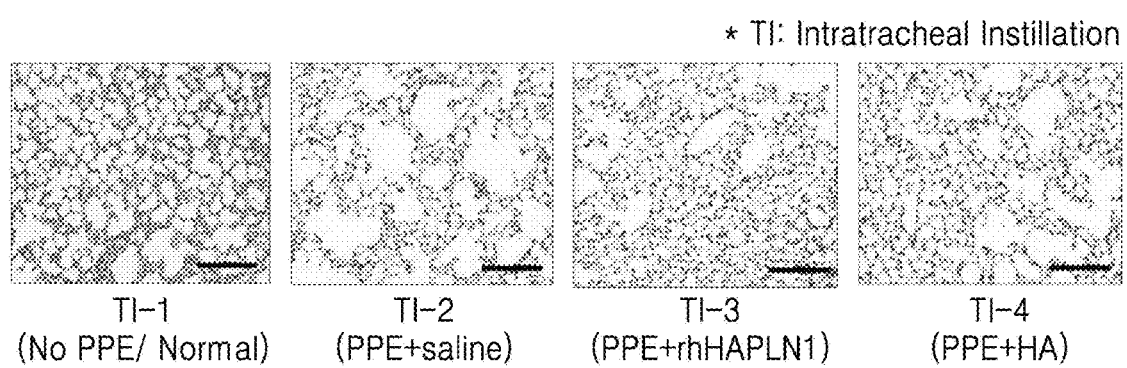
Figure 4B:
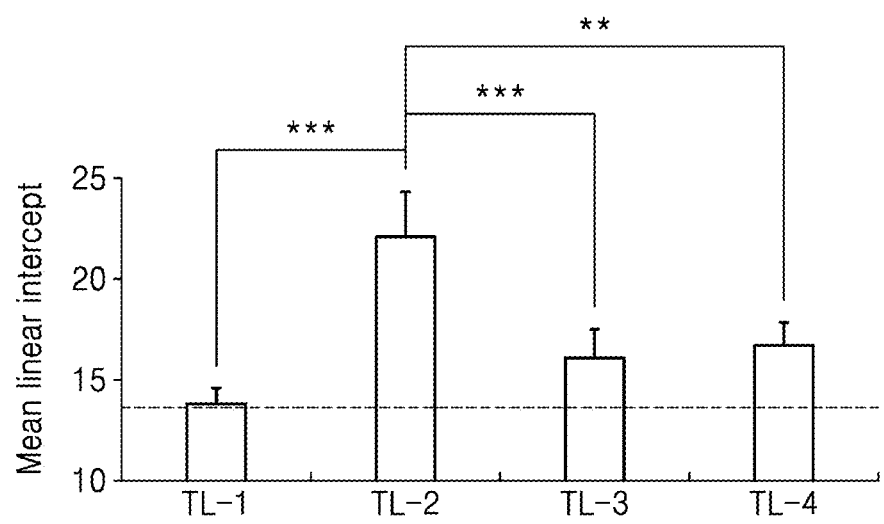
Figure 4C:
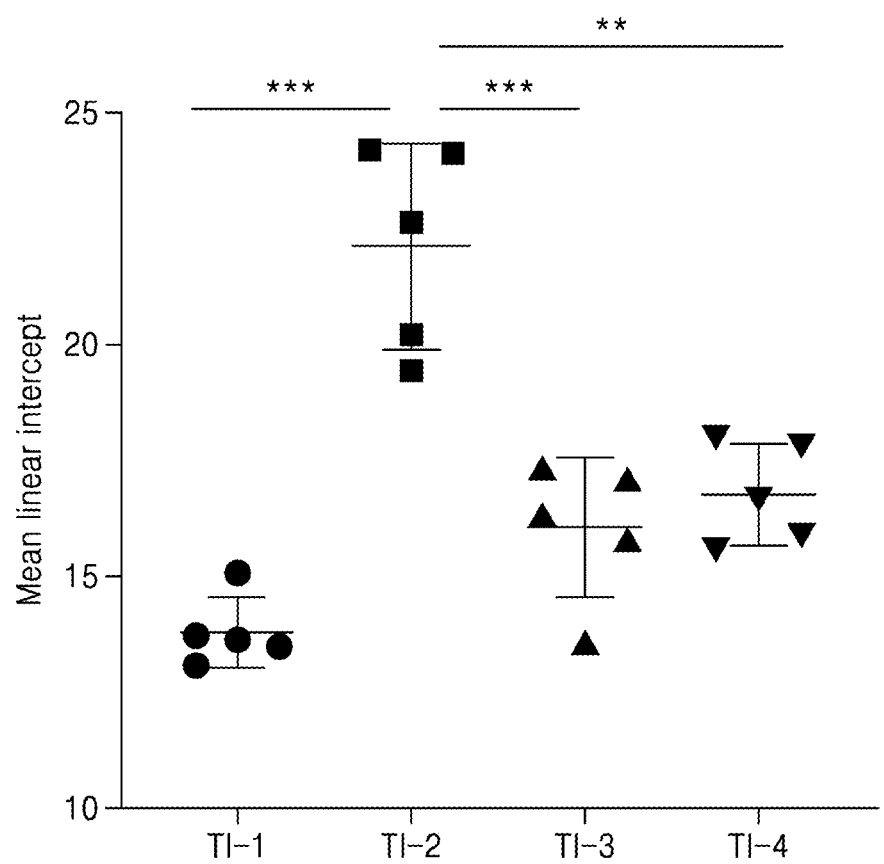

FIG. 4 shows the results of TI groups, and referring to FIGS. 4A to 4C, the PPE-treated group (TI-2) of 22.1 μm showed about 1.6 times increase, as compared with the untreated normal group (TI-1) of 13.8 μm (p<0.001). The rhHAPLN1-treated group (TI-3) of 16.1 μm showed about 72% reduction, as compared with the PPE-treated group (TI-2) of 22.1 μm (p<0.0009).

In contrast, from the viewpoint of concentration, the HA-treated group (TI-4) of 5.71% (w/v) which was about 17 times higher than 0.33% (w/v) showed about 64% reduction (p<0.00123), indicating that the positive control HA treatment also showed slightly lower efficacy than the rhHAPLN1 treatment which showed about 72% reduction.

A recombinant HAPLN1 according to the present disclosure may have superior effects of improving alveolar damage caused by aging or elastin reduction, and thus it may be used as a pharmaceutical composition or a health functional food composition for preventing or treating pulmonary diseases, such as chronic bronchitis, asthma, emphysema, chronic obstructive pulmonary disease, etc., which are caused by aging or elastin reduction.

What is claimed is:

1. A method of treating pulmonary disease, comprising administering to a subject in need thereof a pharmaceutical composition comprising hyaluronan and proteoglycan link protein 1 (HAPLN1) protein, wherein the pulmonary disease is chronic bronchitis, asthma, emphysema, or chronic obstructive pulmonary disease (COPD), the HAPLN1 protein comprises SEQ ID NO: 1, and the pharmaceutical composition improves alveolar damage caused by aging or elastic reduction.

2. The method of claim 1, wherein the pulmonary disease is COPD.

3. The method of claim 1, wherein the pulmonary disease is chronic bronchitis.

4. The method of claim 1, wherein the pulmonary disease is emphysema.

5. The method of claim 1, wherein the pulmonary disease is asthma.

6. The method of claim 1, comprising administering the HAPLN1 protein, wherein the HAPLN1 protein is recombinant HAPLN1 protein.

7. The method of claim 6, wherein the recombinant HAPLN1 protein is recombinant human HAPLN1 (rhHAPLN1) protein.

8. The method of claim 2, comprising administering the HAPLN1 protein, wherein the HAPLN1 protein is recombinant HAPLN1 protein.

\* \* \* \* \*